(12) United States Patent
Shen et al.

(10) Patent No.: US 11,390,845 B2
(45) Date of Patent: Jul. 19, 2022

(54) METHODS OF MANUFACTURING AND ASSEMBLING CELL-CONTAINING BLOCKS

(71) Applicant: Asia University, Taichung (TW)

(72) Inventors: Yu Fang Shen, Taichung (TW); Ming You Shie, Taichung (TW); Yi Wen Chen, Taichung (TW); Wei Huang Wang, Taichung (TW)

(73) Assignee: Asia University, Taichung (TW)

( * ) Notice: Subject to any disclaimer, the term of this patent is extended or adjusted under 35 U.S.C. 154(b) by 455 days.

(21) Appl. No.: 16/446,802

(22) Filed: Jun. 20, 2019

(65) Prior Publication Data
US 2019/0390162 A1     Dec. 26, 2019

(30) Foreign Application Priority Data

Jun. 21, 2018 (TW) .................................. 107121205

(51) Int. Cl.
    *C12N 5/00*         (2006.01)
    *B33Y 10/00*       (2015.01)
    *B33Y 80/00*       (2015.01)

(52) U.S. Cl.
    CPC ............ *C12N 5/0068* (2013.01); *B33Y 10/00* (2014.12); *B33Y 80/00* (2014.12); *C12N 2500/14* (2013.01); *C12N 2533/30* (2013.01); *C12N 2533/54* (2013.01); *C12N 2535/00* (2013.01)

(58) Field of Classification Search
    CPC .............. C12N 5/0068; C12N 2500/14; C12N 2533/30; C12N 2533/54; C12N 2535/00; B33Y 10/00; B33Y 80/00
See application file for complete search history.

(56) References Cited

U.S. PATENT DOCUMENTS

| | | | |
|---|---|---|---|
| 8,137,563 B2* | 3/2012 | Ma ......................... | B01J 20/291 210/656 |
| 8,361,781 B2* | 1/2013 | Morgan .................. | C12M 21/08 435/288.1 |
| 2015/0375453 A1* | 12/2015 | Yost ....................... | B29C 64/393 435/174 |

OTHER PUBLICATIONS

Hwang et al. Fabrication of three-dimensional porous cell-laden hydrogel fortissue engineering. Biofabrication 2 (2010) 035003 (12pp) (Year: 2010).*
Lee et al. 96 Pillar-Well Plate for 3D Cell Culture. 15th International Conference on Miniaturized Systems for Chemistry and Life Sciences (Oct. 2-6, 2011), 1469-1471. (Year: 2011).*

(Continued)

*Primary Examiner* — Sean C. Barron
(74) *Attorney, Agent, or Firm* — Alan D. Kamrath; Karin L. Williams; Mayer & Williams PC

(57) ABSTRACT

Provided is a method for manufacturing cell-containing blocks having steps of: preparing an standardized size mold by 3D printing (three dimensional printing) using a biocompatible elastic material; injecting a thermosensitive colloid into the mold to form a thermosensitive mold; injecting a hydrogel containing cells in to the thermosensitive mold and curing the hydrogel containing cells to form the cell-containing blocks; separating the thermosensitive mold and the cell-containing blocks at a temperature higher than a solidifying point of the thermosensitive colloid. Also provided are method for assembling the cell-containing blocks in a target configuration by using an assembling mold defining the target configuration and made of a thermoreversible material.

14 Claims, 3 Drawing Sheets

(56) References Cited

OTHER PUBLICATIONS

Ahn et al. Cells (MC3T3-E1)-Laden Alginate Scaffolds Fabricated by a Modified Solid-Freeform Fabrication Process Supplemented with an Aerosol Spraying. Biomacromolecules (2012), 13, 2997-3003. (Year: 2012).*

Miller et al. Rapid casting of patterned vascular networks for perfusable engineered three-dimensional tissues. Nature Materials (2012), 11, 768-774. (Year: 2012).*

Kim et al. Strategy to Achieve Highly Porous/Biocompatible Macroscale Cell Blocks, Using a Collagen/Genipin-bioink and an Optimal 3D Printing Process. ACS Appl. Mater. Interfaces (2016), 8, 32230-32240. (Year: 2016).*

Gurkan et al. Emerging Technologies for Assembly of Microscale Hydrogels. Adv. Healthcare Mater. (2012), 1, 149-158. (Year: 2012).*

Kang et al. Cell encapsulation via microtechnologies. Biomaterials 35 (2014) 2651-2663. (Year: 2014).*

Zhu et al. 3D printing of functional biomaterials for tissue engineering. Current Opinion in Biotechnology (2016), 40:103-112. (Year: 2016).*

Hung et al. Synthesis and 3D Printing of Biodegradable Polyurethane Elastomer by a Water-Based Process for Cartilage Tissue Engineering Applications. Adv. Healthcare Mater. (2014), 3, 1578-1587. (Year: 2014).*

Muller et al. Printing Thermoresponsive Reverse Molds for the Creation of Patterned Twocomponent Hydrogels for 3D Cell Culture. (2013), 77, e50632, 9 pages. (Year: 2013).*

\* cited by examiner

METHODS OF MANUFACTURING AND ASSEMBLING CELL-CONTAINING BLOCKS

BACKGROUND OF THE INVENTION

1. Field of the Invention

The present invention is related to a bioprinting manufacture method, particularly to a method of manufacturing cell-containing blocks and a method of assembling the same.

2. Description of Related Art

Three important components of the scaffold-free bioprinting are bioinks, biopaper, and bioprinter. Biopaper is used as a matrix, such as collagen and nutrient sources. Bio-ink is a self-assembly of three-dimensional cell/tissue spheres, which is also the most important component among others. Bioprinting is a biological manufacturing technology that has emerged in recent years. Studies have shown that, compared to cells cultured in two-dimensional medium, three-dimensional tissue spheres have more benefits, such as closer to the stereoscopic state of the living tissue, which are useful for advancing the comprehensive knowledge of tissues for the researcher.

The three-dimensional tissue spheres to be applied to tissue engineering and organ printing are obligated to conform to appropriate standards and requirements. The requirements for said three-dimensional tissue spheres include, but not limited to: first, being able to be efficiently expanded to achieve rapid production; secondly, having standardized size in order to prevent them from blocking or destroying the nozzle during their processing or passing through the nozzle of the bioprinter; thirdly, manufacturing methods thereof not able to induce significant cell damage and/or gene (DNA) damage; and fourthly, manufacturing methods thereof not able to impair its ability to integrate into tissues. In addition to the foregoing requirements, manufacturing methods thereof are preferably flexible enough to produce a complex composite structure to achieve a variety of three-dimensional tissue spheres.

Although there are various available methods for preparing the three-dimensional tissue spheres, their population can neither be effectively and rapidly expanded nor be homogeneous, and their spherical shape is not suitable for stacking to form a complicated target configuration, which are problems to be solved.

To overcome the shortcomings, the present disclosure provides methods of manufacturing cell-containing blocks being homogenous and having a standardized size to mitigate or obviate the aforementioned problems.

SUMMARY OF THE INVENTION

In order to solve the above problems that the manufacturing method of the current three-dimensional tissue spheres cannot be rapidly expanded and having a uniform size, the present disclosure provides a method for manufacturing cell-containing blocks, which comprises the steps of:

providing a standardized size mold by three-dimensional printing with a biocompatible elastic material, wherein the standardized size mold is provided with a plurality of protruding blocks;

injecting a thermosensitive colloid into the standardized size mold to form a thermosensitive mold having plurality of recesses, the recesses correspond to the protruding blocks of the standardized size mold;

injecting a hydrogel containing cells into the recesses and curing the hydrogel containing cells to form cell-containing blocks; and converting thermosensitive mold into a liquid colloidal state by incubating the thermosensitive mold together with the cell-containing blocks at a temperature higher than the solidifying point of the thermosensitive colloid, so that the cell-containing blocks are released from the thermosensitive mold to separate the cell-containing blocks.

In some embodiments, each protruding block is dependently or independently in a shape of rectangular cuboid, cube, triangular pyramid, polyhedron or sphere.

In some embodiments, the thermosensitive colloid is gelatin or collagen.

In some embodiments, the biocompatible elastic material is a hydrophilic polyurethane or an amine-based resin.

In some embodiments, the step of preparing a hydrogel containing cells comprises mixing gelatin or collagen with a hydrogel containing sodium alginate and cells; and the step of curing the hydrogel containing cells further comprises adding a calcium chloride solution, so that the calcium ion reacts with the sodium alginate to maintain the hydrogel containing cells in a state of solidification.

In some embodiments, the step of incubating the thermosensitive mold together with the cell-containing blocks are performed at a temperature higher than a solidifying point of the thermosensitive colloid, and alternatively lower than a solidification temperature of the hydrogel containing cells.

In some embodiments, the step of converting the thermosensitive mold into a liquid colloidal state further comprises placing the thermosensitive mold together with the cell-containing blocks in a culture media containing calcium chloride.

In one aspect, the present disclosure provides a method for assembling cell-containing blocks, which comprises the steps of:

preparing an assembling mold with a structure defining a target configuration by three-dimensional printing using a thermosensitive colloid;

applying a second hydrogel onto surfaces of the cell-containing blocks according to the present disclosure, stacking the applied cell-containing blocks into the target configuration and curing the second hydrogel to form an assembly of the cell-containing blocks, wherein the second hydrogel comprises gelatin and sodium alginate;

placing the assembling mold together with the assembly of the cell-containing blocks in an environment to convert the thermosensitive colloid into to a liquid colloidal state to separate the assembly of the cell-containing blocks.

In some embodiments, the steps of applying the second hydrogel and stacking the applied cell-containing blocks are performed by using a bioprinter.

In another aspect, the present disclosure also provides a method for assembling cell-containing blocks, which comprises the steps of:

preparing an assembling mold with a structure defining a target configuration by three-dimensional printing using a thermoreversible material, the thermoreversible material is provided with being in a solid state at a high temperature and in a liquid state at a low temperature;

stacking the cell-containing blocks according to the present disclosure into the target configuration and conjugating cell-containing blocks by allowing cells therein being self-attached or attaching to cells in adjacent cell-containing blocks to form an assembly of the cell-containing blocks; and placing the assembling mold together with the assembly of the cell-containing blocks at the low temperature to convert the thermoreversible material into to a liquid state to separate the assembly of the cell-containing blocks;

wherein the thermoreversible material comprises poly (ethylene oxide)-polypropylene oxide)-poly(ethylene oxide) triblock copolymer (PEO-PPO-PEO Triblock Copolymer, Pluronic® F127.)

Based on the above description, the methods according to the present disclosure has the following advantages.

First, the method for manufacturing cell-containing blocks according the present disclosure utilizes a standardized mold by three-dimensional printing, so that the prepared cell-containing blocks have an uniform size, conforming to requirement of standardized size, and suitable for rapid and large-scale production, and the use of biocompatible materials during the entire process, avoiding the induction of significant cell damage and/or genetic (DNA) damage or hamper to its ability to integrate into tissues.

Further, the present invention utilizes the characteristics of the thermoreversible materials can be converted to a solidified state or a liquid state at specific temperatures, and are suitable for manufacturing of cell-containing blocks with a stereoscopic structure being more complicated than the existing three-dimensional tissue spheres, without requiring forced demolding. After molding or drafting, it can be smoothly demolded and removed to maintain the integrity of the three-dimensional structure of the cell-containing blocks, which is more advantageous to be subject to subsequent complex tissue assembly and stacking.

Other objectives, advantages and novel features of the methods according to the present disclosure will become more apparent from the following detailed description when taken in conjunction with the accompanying drawings.

DETAILED DESCRIPTION OF THE PREFERRED EMBODIMENT

Figure 1:
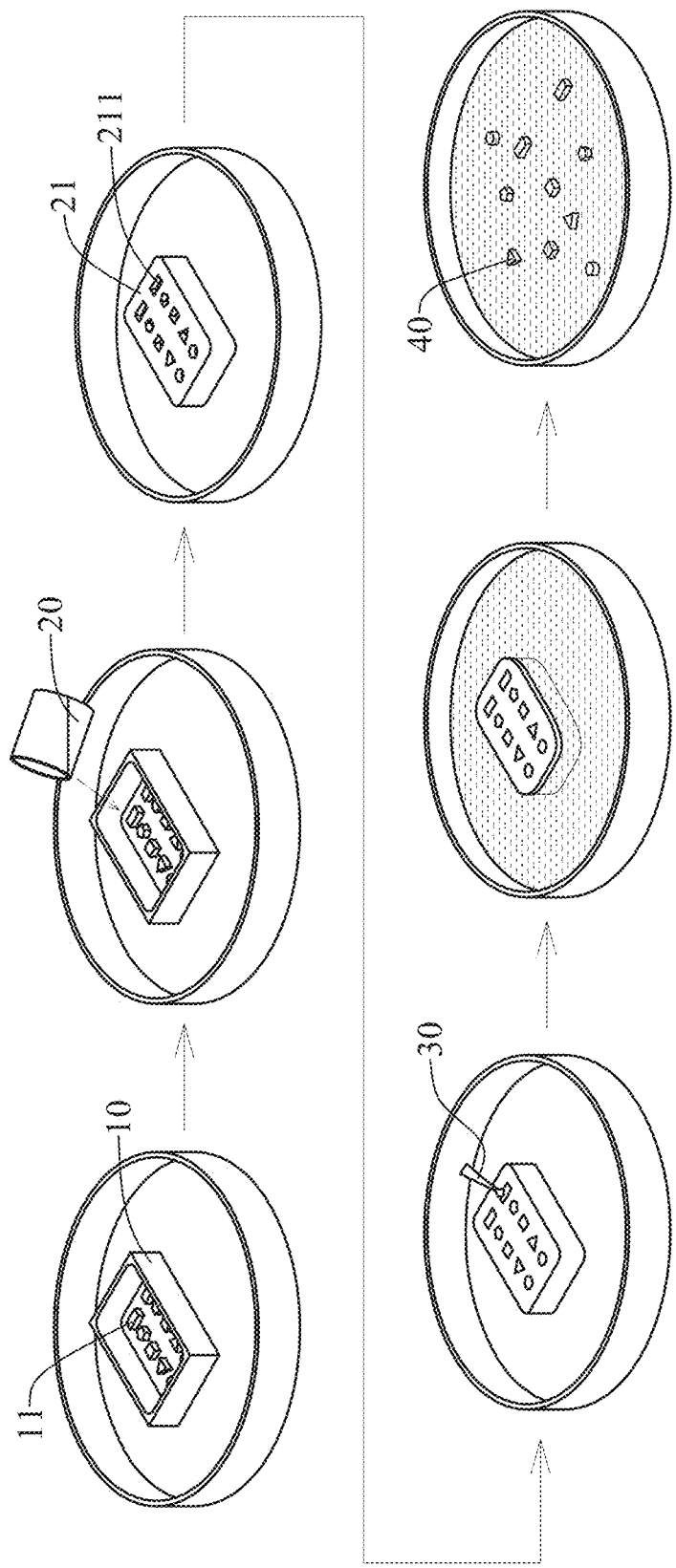
FIG. 1 is a flow chart showing a preferred embodiment of a method for manufacturing cell-containing blocks according to the present disclosure.

Reference will now be made in detail to the present preferred embodiments of the invention, examples of which are illustrated in the accompanying drawings. Wherever possible, the same reference numbers are used in the drawings and the description to refer to the same or like parts. It is not intended to limit the method by the exemplary embodiments described herein. In the following detailed description, for purposes of explanation, numerous specific details are set forth in order to attain a thorough understanding of the disclosed embodiments. It will be apparent, however, that one or more embodiments may be practiced without these specific details. As used in the description herein and throughout the claims that follow, the meaning of "a", "an", and "the" may include reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "inject", "injecting", "pour" or "pouring" will be understood as the material is introduced into mold(s), which can be equally substituted by "instill" or "infuse". As used in the description herein and throughout the claims that follow, the meaning of "stack", "stacking" will be understood as the material is arranged into certain three dimensional structure, which also can be equally substituted by "pile".

As shown in FIG. 1, the present disclosure provides a method for manufacturing cell-containing blocks, the steps comprising:

Step 1: using an elastic biocompatible material, such as hydrophilic polyurethane or amine-based resin, printing a standardized size mold 10 by three-dimensional printing so that the standardized size mold 10 is provided with a plurality of protruding blocks 11 having different three-dimensional shapes. As shown in this embodiment, the protruding blocks 11 are in a shape including rectangular cuboid, cube, triangular pyramid, polyhedron or sphere and the like;

Step 2: injecting a thermosensitive colloid 20, such as gelatin, collagen, etc., into the standardized size mold 10, and after the thermosensitive colloid 20 being cooled and solidified to be drawn out as a thermosensitive mold 21 with a plurality of recesses 211 having different three-dimensional shapes corresponding to the protruding blocks 11 of the standardized size mold 10; since the standardized size mold 10 has elasticity and the standardized size mold 10 could be squeezed or slightly deformed to facilitate removal of the formed thermosensitive mold 21 after solidification, the thermosensitive mold 21 was prevented from being damaged during the process of drawing out;

Step 3: injecting a hydrogel containing cells 30 into the recess 211 and curing it as allowing it to solidify; and Step 4: placing the solidified hydrogel containing cells 30 together with the thermosensitive mold 21 at a temperature higher than the thermosensitive colloid 20, wherein the temperature caused the thermosensitive colloid 20 to convert from a solidified state to a liquid colloidal state, and the hydrogel containing cells 30, which remains in a solidified state, could be released from the thermosensitive mold 21 without a forcedly drawing therefrom to obtain the cell-containing blocks 40 according the present disclosure.

As described above, formulation of the hydrogel containing cells 30 of the present disclosure was preferably obtained by mixing 5-20% gelatin or collagen with a hydrogel containing 0.5-2% (preferably 1.2%) sodium alginate and cells. The cell-containing hydrogel of the present embodiment preferably has a cell concentration of $10^6$-$10^8$/40 ul, more preferably $10^7$/40 ul, but since the cell concentration was adjusted according to requirements, the cell concentration of the hydrogel containing cells 30 was not limited in accordance with the present disclosure. In accordance with the above formulation, the step of curing the hydrogel containing cells 30 of the foregoing Step 3 further comprises solidifying the gelatin by cooling and simultaneously adding a calcium chloride solution, so that the sodium alginate was solidified by the calcium ion thereof. The coagulation phenomenon of sodium alginate and calcium ions in the hydrogel containing cells 30 would result in that the hydrogel containing cells 30, when admixed with gelatin or collagen with thermosensitive properties, remained in a solidified state in Step 4, even if the thermosensitive mold 21 was converted into a liquid colloidal state, and the effect of release and separation of the same was thus successfully achieved.

In addition, in the Step 4, the step of converting the thermosensitive mold 21 from the solidified state to the liquid colloid state could further comprises depositing the solidified hydrogel containing cells 30 together with the thermosensitive mold 21 in a culture media containing calcium chloride solution, when the thermosensitive mold 21 was converted into a liquid colloidal state at a specific temperature, the released hydrogel containing cells 30 was immediately immersed in the culture media containing calcium ions so as to be maintained in a solidified state. After a period of time, the cells in the cells will grow and differentiate on their own and connect to each other, so that they can maintain the shape of the formation without immersing in the culture solution containing calcium ions.

Figure 2:
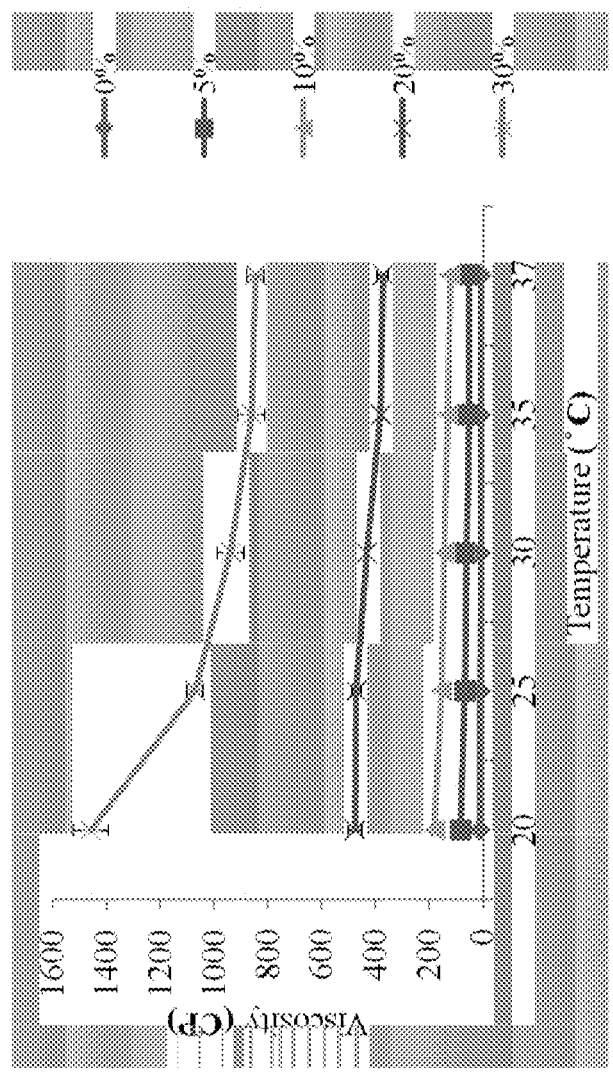
FIG. 2 is a graph showing the viscosity of the hydrogels containing cells of the present disclosure with different contents at various temperatures.

Then, since the viscosity of the used materials was a key parameter for subsequent bio-printing, and the temperature and formulation of materials would affect the viscosity of the materials, as shown in FIG. 2, determined was viscosity of the hydrogel containing cells 30 according to the present disclosure in conditions of having various components at different proportions and at different temperatures, in addition adding up 0, 5, 10, 15, 20% gelatin into the hydrogel containing 1.2% sodium alginate and being deposited at 20, 25, 30, 35 and 37° C. by using a microcomputer digital viscometer DV1 (Brookfield, USA). FIG. 4 shows the results of viscosity assay at different concentrations and temperatures. The viscosity was preferably less than 1000 CP, which has higher fluidity and suitable for operation.

Figure 3:
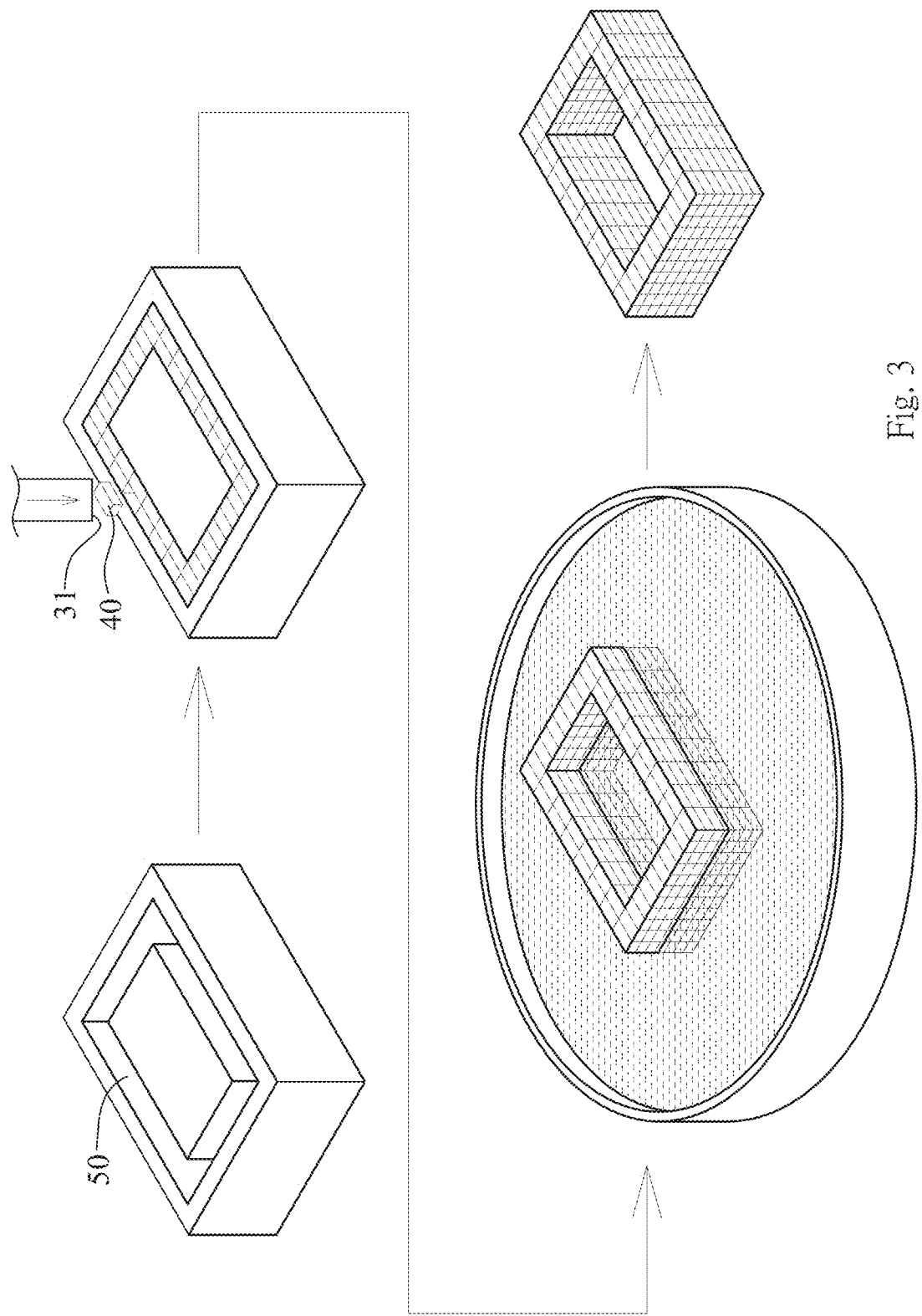
FIG. 3 is a scheme of a preferred embodiment of a method for assembling the cell-containing blocks of the present disclosure.

Further, referring to FIG. 3, a first preferred embodiment of the method for assembling the cell-containing blocks prepared by the foregoing manufacturing method according to the present invention, includes the following steps:

Step 1: preparing an assembling mold 50 with a structure defining a target configuration by a three-dimensional printing using a thermosensitive colloid 20, such as gelatin or collagen;

Step 2: stacking the cell-containing blocks 40 in the target configuration after applying a second hydrogel 31 onto their surfaces to allow the second hydrogel 31 curing and the surfaces to be firmly attached each other to form, wherein the second hydrogel 31 preferably comprises gelatin/collagen and sodium alginate, and the curing of hydrogel was directed to immersing the assembling mold 50 together with the cell-containing blocks 40 therein into a calcium chloride solution, and the sodium alginate in the second hydrogel 31 would react with calcium ions in the solution to solidify;

Step 4: placing the assembling mold 50 together with the cell-containing blocks 40 therein at a temperature higher than the solidifying point of the thermosensitive colloid 20 to convert the thermosensitive colloid 20 into to a liquid colloidal state to release an assembly of the cell-containing blocks 40 therefrom.

Accordingly, the applying of the second hydrogel 31 and the stacking steps as described above could be carried out by using a bioprinter, mainly the cell-containing blocks 40 applied with the second hydrogel 31 were directly extruded into the assembling mold 50 with a structure defining a target configuration or even in a target tissue with defect from the bioprinter to achieve the purpose of repairing target tissue.

A second preferred embodiment of the method for assembling cell-containing blocks, which comprises the steps of:

Step 1: preparing an assembling mold 50 with a structure defining a target configuration by three-dimensional printing using a thermoreversible material (low temperature liquid, high temperature curing), such as poly(ethylene oxide)-polypropylene oxide)-poly(ethylene oxide) triblock copolymer (PEO-PPO-PEO Triblock Copolymer, Pluronic® F127, hereinafter F127);

Step 2: stacking the cell-containing blocks 40 in the target configuration inside the assembly mold 50, followed by allowing cells therein being self-attached or attaching to cells in adjacent cell-blocking blocks 40;

step 3: placing the assembling mold 50 together with the cell-containing blocks 40 at a low temperature to convert the thermosensitive mold 50 (for F127, in a condition of about 4° C. for 5 minutes) into a liquid colloid state an assembly of the cell-containing blocks 40 could be released.

In addition, when three-dimensional printing was utilized, the standardized size mold 10 and the thermosensitive mold 50 were mutually corresponding, the cell-containing blocks 40 thus formed could be effectively stacked and assembled into the target configurations. The cell-containing blocks 40 of the present disclosure are not limited to be in a spherical shape, and suitable for adjusting the shape thereof according to the defect region of the target tissue to produce cell-containing blocks more conforming to the shape of said defect region, which results in advantages of assembling and stacking to increase the strength of the overall structure of the assemblies.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method for manufacturing cell-containing blocks, comprising the steps of:
   providing a mold, the mold having a size which does not block a nozzle of a three-dimensional printer, by three-dimensional printing with a biocompatible material, wherein the mold is provided with a plurality of protruding blocks;
   injecting a thermosensitive colloid into the mold to form a thermosensitive mold having plurality of recesses, wherein the plurality of recesses corresponds to the plurality of protruding blocks of the mold;
   injecting a hydrogel containing cells into the plurality of recesses and curing the hydrogel containing cells to obtain cell-containing blocks; and
   converting the thermosensitive mold into a liquid colloidal state by incubating the thermosensitive mold together with the cell-containing blocks at a temperature higher than the solidifying point of the thermosensitive colloid, wherein the cell-containing blocks are mold-released from the thermosensitive mold.

2. The method according to claim 1, wherein each protruding block has different three-dimensional shapes including rectangular cuboid, cube, triangular pyramid, polyhedron or sphere.

3. The method according to claim 1, wherein the thermosensitive colloid is gelatin or collagen.

4. The method according to claim 1, the biocompatible elastic material is a hydrophilic polyurethane or an amine-based resin.

5. The method according to claim 1, wherein the step of preparing a hydrogel containing cells comprises mixing gelatin or collagen with a hydrogel containing sodium alginate and cells; and the step of curing the hydrogel containing cells comprises adding a reacting a calcium chloride solution with the sodium alginate, so that the calcium ion reacts with the sodium alginate to maintain the hydrogel containing cells in a state of solidification.

6. The method according to claim 1, wherein the step of incubating the thermosensitive mold together with the cell-containing blocks are performed at a temperature higher than a solidifying point of the thermosensitive colloid and lower than a solidification temperature of the hydrogel containing cells.

7. The method according to claim 1, wherein the step of converting the thermosensitive mold into a liquid colloidal state further comprises placing the thermosensitive mold together with the cell-containing blocks in a culture media containing calcium chloride.

8. The method according to claim 2, wherein the step of converting the thermosensitive mold into a liquid colloidal state further comprises placing the thermosensitive mold together with the cell-containing blocks in a culture media containing calcium chloride.

9. The method according to claim 3, wherein the step of converting the thermosensitive mold into a liquid colloidal state further comprises placing the thermosensitive mold together with the cell-containing blocks in a culture media containing calcium chloride.

10. The method according to claim 4, wherein the step of converting the thermosensitive mold into a liquid colloidal state further comprises placing the thermosensitive mold together with the cell-containing blocks in a culture media containing calcium chloride.

11. The method according to claim 5, wherein the step of converting the thermosensitive mold into a liquid colloidal state further comprises placing the thermosensitive mold together with the cell-containing blocks in a culture media containing calcium chloride.

12. A method for assembling cell-containing blocks, which comprises the steps of:

preparing an assembling mold with a structure defining a target configuration by three-dimensional printing using a thermosensitive colloid;

applying a second hydrogel onto surfaces of the cell-containing according to claim 1, stacking the applied cell-containing blocks into the target configuration and curing the second hydrogel to form an assembly of the cell-containing blocks, the second hydrogel comprises gelatin and sodium alginate;

placing the assembling mold together with the assembly of the cell-containing blocks in an environment to convert the thermosensitive colloid into to a liquid colloidal state to separate the assembly of the cell-containing blocks.

13. The method according to claim 12, wherein the steps of applying the second hydrogel and stacking the applied cell-containing blocks are performed by using a bioprinter.

14. A method for assembling cell-containing blocks, which comprises the steps of:

preparing an assembling mold with a structure defining a target configuration by three-dimensional printing using a thermoreversible material;

stacking the cell-containing blocks according to claim 1 into the target configuration and conjugating cell-containing blocks by allowing cells therein being self-attached or attaching to cells in adjacent cell-containing blocks to form an assembly of the cell-containing blocks; and placing the assembling mold together with the assembly of the cell-containing blocks at the low temperature to convert the thermoreversible material into to a liquid state to separate the assembly of the cell-containing blocks;

wherein the thermoreversible material comprises poly(ethylene oxide)-poly(propylene oxide)-poly(ethylene oxide) triblock copolymer.

* * * * *